United States Patent [19]

Pfefferkorn

[11] Patent Number: 4,988,346
[45] Date of Patent: Jan. 29, 1991

[54] REAR FASTENING DISPOSABLE DIAPER

[75] Inventor: Jason L. Pfefferkorn, 1529 Woodpine Dr., El Cajon, Calif. 92019

[73] Assignees: Jason L. Pfefferkorn; Ronnie D. Swaim; James H. Evans, all of El Cajon, Calif.

[21] Appl. No.: 361,387

[22] Filed: Jun. 5, 1989

[51] Int. Cl.5 .................................... A61F 13/15
[52] U.S. Cl. ......................................... 604/389
[58] Field of Search .............. 604/386, 389, 390, 391, 604/392, 393, 394, 401; 2/80, 82, 83, 400

[56] References Cited

U.S. PATENT DOCUMENTS

| | | | |
|---|---|---|---|
| 2,497,533 | 2/1950 | Blankenship | 604/386 |
| 2,544,726 | 3/1951 | Rogatz | 604/394 |
| 2,711,736 | 6/1955 | Petitpas | 604/401 |
| 2,833,282 | 5/1958 | Moore | 604/386 |
| 2,931,747 | 4/1960 | Dexter | 154/43 |
| 3,530,859 | 9/1970 | Heimowitz | 604/386 |
| 3,559,648 | 2/1971 | Mason, Jr. | 128/287 |
| 4,034,752 | 7/1977 | Tritsch | 128/184 |
| 4,209,016 | 6/1980 | Schaar | 128/287 |
| 4,210,143 | 7/1980 | De Johckheere | 128/287 |
| 4,253,461 | 3/1981 | Strickland et al. | 128/287 |
| 4,402,690 | 9/1983 | Redfern | 604/391 |
| 4,500,316 | 2/1985 | Damico | 604/389 |
| 4,753,650 | 6/1988 | Williams | 604/389 |
| 4,850,992 | 7/1989 | Amaral et al. | 604/389 |

Primary Examiner—C. Fred Rosenbaum
Assistant Examiner—Sharon Rose
Attorney, Agent, or Firm—Brown, Martin, Haller & McClain

[57] ABSTRACT

A disposable diaper having a fluid permeable inner layer, a fluid impermeable outer layer and an absorbent batt sandwiched between the layers, the diaper having a crotch portion extending between front and rear portions. The rear portion of the diaper is provided with a first securing system affixed to the outer surface of its outer layer so that the rear portion may be secured to the front portion as the diaper is wrapped around a baby. The front portion of the diaper is provided with a second securing system to allow the opposing edges of the front portion to be secured adjacent one another at a location behind the baby's back.

7 Claims, 1 Drawing Sheet

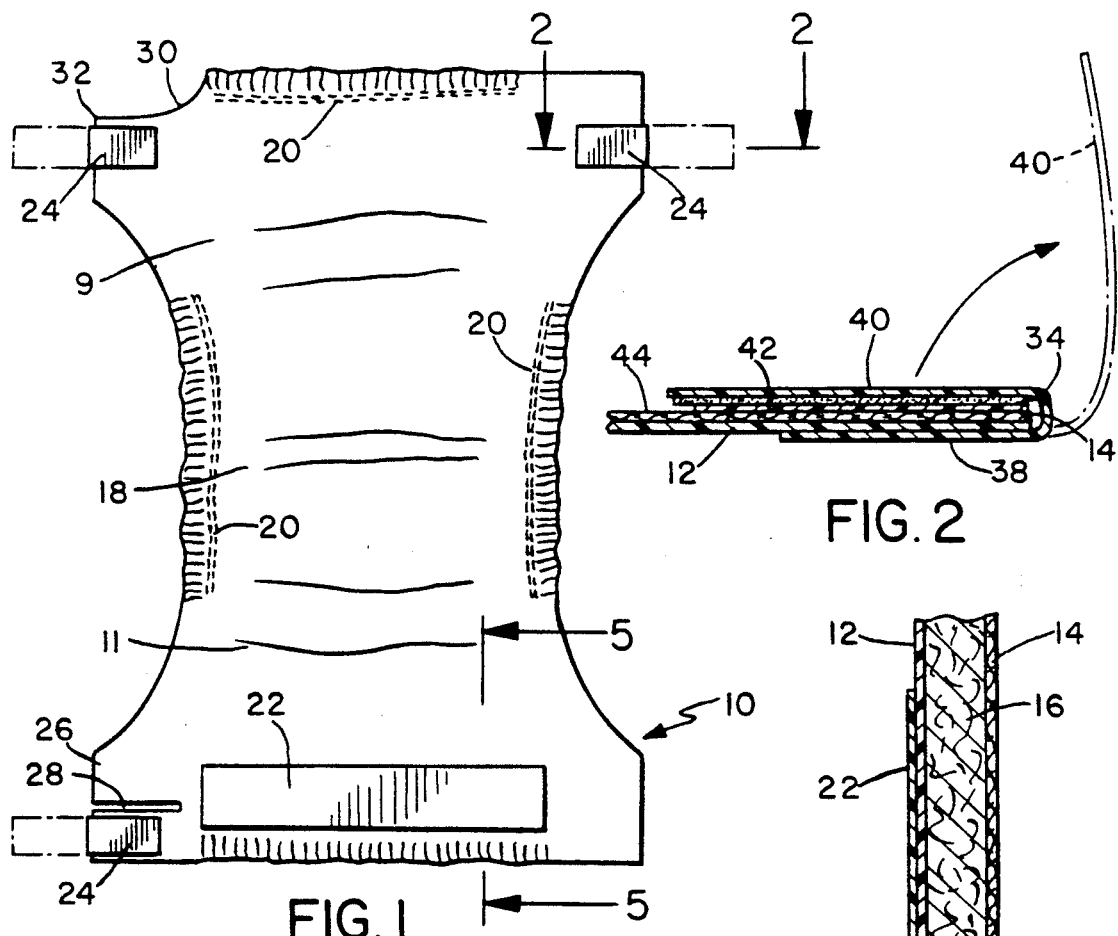
FIG. 2
FIG. 1
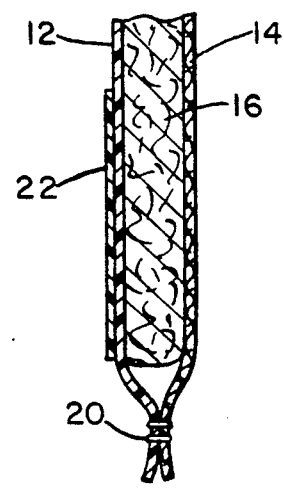
FIG. 5
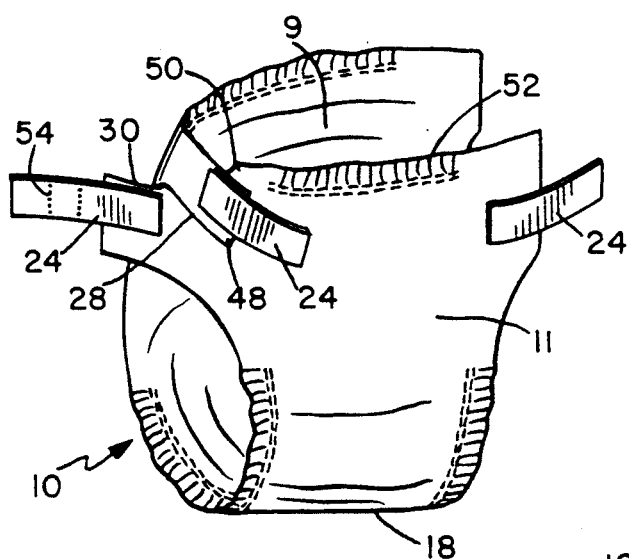
FIG. 3
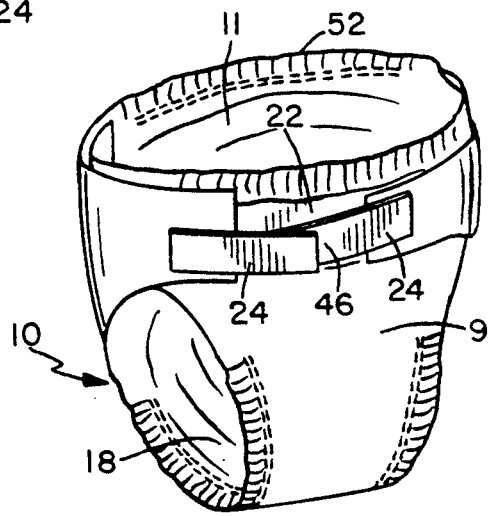
FIG. 4

REAR FASTENING DISPOSABLE DIAPER

BACKGROUND OF THE INVENTION

This invention relates to diapers for infants, and more particularly to diapers intended to be disposed of after a single use.

Disposable diapers of a variety of types have achieved increasing commercial success in the marketplace. Typical disposable diaper configurations include an inner layer that is formed from a moisture permeable material designed for contact with the user. The inner layer is backed by an absorbent material enclosed by a moisture impermeable outer layer, preferably formed of a polyethylene film or other suitable material.

For purposes of convenience and safety, adhesive diaper fastening systems have become quite common. In a conventional disposable diaper configuration, adhesive tape strips are located on the sides of the rear waistband portion of the diaper. The adhesive strips have fixed ends permanently adhered to the outer layer of the diaper. The exposed ends of the adhesive strips are generally protected by cover strips that can be readily removed when placing the diaper on an infant, thus exposing the adhesive surfaces of the strips. When the diaper is applied to the infant, the adhesive strips and associated portions of the rear waistband portion are drawn around the infant's waist and secured to respective sides of the front portion of the diaper. This configuration has the disadvantage in that the locations of the adhesive strips are accessible to the prying hands of the infant once the diaper is in place. As a result, the infant may loosen or remove the diaper at an inopportune time.

An illustrative prior art adhesive system is disclosed in U.S. Pat. No. 4,753,650 to Williams. The Williams arrangement has the disadvantage of having the adhesive tapes located at positions readily accessible to the infant when the diaper is in place, i.e., at the sides of the infant.

SUMMARY OF THE INVENTION

In accordance with the present invention, an adhesive strip fastening system for a disposable diaper having an absorbent batt sandwiched between a moisture-permeable inner layer and a moisture-impermeable outer layer includes a first securing means for attaching the rear portion of the diaper to the front portion of the diaper to retain the position of the diaper on the infant while the sides of the front portion of the diaper are secured adjacent one another when wrapped around the rear portion of the diaper and secured by a second securing means.

In a preferred arrangement, the first securing means comprises an adhesive tape strip having one end permanently affixed to a corner of the rear portion of the diaper, and intended for adhesively connecting to the outer layer of the front portion of the diaper.

Moreover, the second securing means preferably comprises elongated adhesive tape strips, each having one end permanently affixed to opposing sides of the front portion of the diaper and adapted for overlapping and adhering to one another as the sides of the front portion of the diaper are wrapped around the rear portion of the diaper. The adhesive strip configuration of the present invention locates the primary diaper securing point behind the infant, thus limiting or eliminating the infant's access to the securing point.

BRIEF DESCRIPTION OF THE DRAWINGS

The features and advantages of the present invention will become more apparent from the description provided herein when viewed in conjunction with the drawings in which like reference characters correspond and throughout wherein, FIG. 1 is a perspective view of an open unfolded disposable diaper in accordance with one embodiment of the invention;

FIG. 2 is an enlarged sectional view taken on line 2—2 of FIG. 1 showing the layered construction of the diaper with adhesive tape strip attached;

FIG. 3 is a front perspective view of the diaper in the use configuration;

FIG. 4 is a rear perspective view of the diaper of FIG. 1 in the use configuration; and FIG. 5 is an enlarged sectional view taken on line 5—5 of FIG. 1.

DESCRIPTION OF THE PREFERRED EMBODIMENT

Disposable diaper 10, illustrated in FIGS. 1 and 5 comprises a moisture impermeable polyethylene outer layer 12, a moisture permeable inner layer 14 formed of bonded polypropylene filaments or other suitable nonwoven fibrous or filamentous material, and a moisture retaining absorbent batt 16, enclosed between the outer and inner layers. The outer and inner layers are generally coextensive with one another and somewhat larger than the absorbent batt and are bonded together around the periphery of the diaper by heat bonding or other convenient bonding methods.

The outer and inner layers are shaped to provide a narrow crotch region 18 extending between front and rear end portions 11 and 9. Elastic threads 20 formed of natural rubber or other suitable elastomeric material are provided adjacent the sides of the crotch region for gathering the diaper and forming a moisture seal around the infant's legs. Additional elastic threads are provided adjacent the ends of the diaper for forming a moisture seal around the infant's waist. The diaper is generally rectangular in shape with opposite corner portions at each end portion of the diaper extending outwardly from a central area aligned with the crotch region.

Release region 22 is provided on the outer surface of the outer layer and located adjacent at least one end of the diaper. Said release region is preferably formed of a smooth, nontextured polyvinyl plastic strip or other suitable material to facilitate relocation of adhesive tape strips 24, during the diapering process. Release region 22 provides a durable surface on which the adhesive strips may be selectively attached and detached without damage to the outer layer of the diaper.

Side edge 26 of the front portion of diaper 10 has an inward-extending slit 28 intermediate the adhesive tape strip 24 and crotch region 18. Said side edge is further provided with notch 30 located at the corner 32 opposite said slit for cooperation therewith.

FIG. 2 illustrates a typical adhesive tape strip 24, placed along an edge of the outer layer of the diaper. The adhesive tape strip 24 may be formed of polyvinyl plastic or other suitable durable material and is preferably coated with pressure sensitive adhesive 34 on its inner surface adhesive tape strip 24 has anchoring portion 38 and attaching portion 40. Anchoring portion 38 is adhesively secured to the outer surface of the outer layer of the diaper. Release strip 42 formed of a smooth nontextured polyvinyl plastic or other suitable material is located on the outer surface 44 of the inner layer 14 such that the attaching portion of the adhesive tape 40 strip overlaps the release strip 42 as the attaching portion 40 is folded around the edge of the diaper 10. In use, the attaching portion 40 is detached from the release strip 42, thereby exposing the adhesive for securing the attaching portion at a suitable position on the diaper, including the nonadhesive surface 46 of a corresponding adhesive tape strip.

FIGS. 3 and 4 show the diaper in use. The baby (not shown for illustration purposes) is laid on its back with its behind placed on the inner layer 14 of the rear portion 9 of the diaper 10. Rear corner 48, bearing adhesive tape strip 24, is wrapped over the corresponding front corner portion 50, of the front portion of the diaper and adhesive tape strip 24 borne on the rear corner 48 is secured to the front portion in the vicinity of front waistband 52. This overlap is facilitated by cooperation of notch 30 with slit 28. The baby is then turned 180 onto its belly.

As viewed in FIG. 4, the opposing rear corners of the rear portion of the diaper are wrapped around the sides of the baby and secured adjacent one another at the rear of the baby by the adhesive tape strips anchored to the rear corners of the diaper. Selected adhesive tape strip 24 may be detached from release strip 42, allowing said adhesive tape strip 24 to be releasably secured to release region 22. Remaining adhesive bearing tape strip 24 is then detached from release strip 42 for adhesive securement to the nonadhesive surface 46 of the corresponding adhesive tape strip 24. Preferably, the adhesive tape strips are provided with at least one set of perforations 54 to allow easy separation of the strips during removal of the diaper for disposal. As illustrated in FIG. 3, the set of perforations across the width of adhesive strip 24 is located in an area which will normally not be affixed to the other strip 24. Although only one of the strips 24 at the front end of the diaper is shown to have lines of perforations 54, it will be understood that such perforations may be provided in non-affixed areas of the opposite strip 24.

The previous description of the preferred embodiment is provided to enable any person skilled in the art to make or use the present invention. Various modifications to this embodiment will be readily apparent to those skilled in the art, and the generic principals defined herein may be applied to other embodiments without the use of the inventive facility. Thus, the present invention is not intended to be limited to the embodiment shown herein, but is to be accorded the widest scope consistent with the principals and novel features disclosed herein.

I claim:
1. A disposable diaper, comprising:
a multi-layer, generally rectangular body member having a fluid impermeable outer layer, a fluid permeable inner layer, and an absorbent batt sandwiched between said outer and inner layer;
the body member having opposite end portions and a crotch portion of reduced width extending between said end portions, said end portions comprising the front and rear portions of the diaper when in use;
each end portion having a central area aligned with said crotch portion and outwardly projecting opposite corner portions;
first securing means projecting from the outer edge of only one of the corner portions of said rear end portion for securing said corner portion to the front end portion to hold the diaper on a wearer; and
second securing means projecting from the outer edge of each of the corner portions of said front end portion for securing said corner portions to the central area of said rear portion at a location behind the wearer's back, said first and second securing means at least at said one side being offset and at least one of said front and rear corner portions at said one side having a cut-out adjacent its respective securing means for allowing said first and second securing means to be overlapped and separately secured to the opposite end portions of the diaper.

2. A disposable diaper comprising:
a multi-layer, generally rectangular body member having a fluid impermeable outer layer, a fluid permeable inner layer, and an absorbent batt sandwiched between said outer and inner layer;
the body member having opposite end portions and a crotch portion of reduced width extending between said end portions, said end portions comprising the front and rear portions of the diaper when in use;
each end portion having a central area aligned with said crotch portion and outwardly projecting opposite corner portions;
first securing means projecting from the outer edge of at least one of the corner portions of said rear end portion for securing said corner portion to the front end portion to hold the diaper on a wearer;
second securing means projecting from the outer edge of each of the corner portions of said front end portion for securing said corner portions to the central area of said rear portion at a location behind the wearer's back, said first and second securing means at least at said one side being offset and at least one of said front and rear corner portions at said one side having a cut-out adjacent its respective securing means for allowing said first and second securing means to be overlapped and separately secured to the opposite end portions of the diaper; and
one of said front and rear corner portions at said one side having a first cut-out adjacent the upper edge of said securing means and the other corner portion at said one side having a second cut-out adjacent the lower edge of its securing means for enabling said side portions to be overlapped.

3. The diaper as claimed in claim 2, wherein at least one of said cut outs comprises an inwardly projecting slit.

4. The diaper as claimed in claim 2, wherein said first cut out comprises an arcuate notch extending along the upper edge of said corner portion towards said central area.

5. A disposable diaper as claimed in claim 1, wherein said first securing means comprises a first elongated adhesive tape strip secured to one corner portion of said rear portion of said diaper.

6. A disposable diaper comprising:
a multi-layer, generally rectangular body member having a fluid impermeable outer layer, a fluid permeable inner layer, and an absorbent batt sandwiched between said outer and inner layer;

the body member having opposite end portions and a crotch portion of reduced width extending between said end portions, said end portions comprising the front and rear portions of the diaper when in use;

each end portion having a central area aligned with said crotch portion and outwardly projecting opposite corner portions;

first securing means projecting from the outer edge of at least one of the corner portions of said rear end portion for securing said corner portion to the front end portion to hold the diaper on a wearer;

second securing means projecting from the outer edge of each of the corner portions of said front end portion for securing said corner portions to the central area of said rear portion at a location behind the wearer's back, said first and second securing means at least at said one side being offset and at least one of said front and rear corner portions at said one side having a cut-out adjacent its respective securing means for allowing said first and second securing means to be overlapped and separately secured to the opposite end portions of the diaper; and said second securing means comprising a pair of elongated adhesive tape strips secured to outer side edges of said corner portions of said front portion of said diaper, said adhesive strips comprising means for overlapping and adhering to one another at least at their outermost ends at said central area of said rear portion of said diaper.

7. A disposable diaper as claimed in claim 6 wherein said adhesive strips are provided with at least one set of perforations across their width.

* * * * *